Jan. 26, 1937.

R. H. McKEE

Plant Pat. 229

HYBRID POPLAR

Original Filed Aug. 26, 1930

Ralph H. McKee
Inventor

Attorney
C. R. Parker, Jr.

Patented Jan. 26, 1937

Plant Pat. 229

UNITED STATES PATENT OFFICE

229

HYBRID POPLAR

Ralph H. McKee, New York, N. Y., assignor to McKee Poplar Forestation, Inc., New York, N. Y., a corporation of New York Original application August 26, 1930, Serial No. 477,979. Divided and this application May 13, 1935, Serial No. 21,254

1 Claim. (Cl. 47—59)

Figure 1:
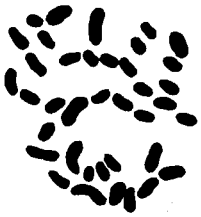

This invention relates to a new and distinct hybrid poplar and more particularly to a hybrid poplar which has a very rapid rate of growth, which is substantially immune to the ordinary diseases to which poplars are susceptible, and the wood of which is particularly suitable for use in making paper pulp.

This is a division of my copending application Serial No. 477,979, filed August 26, 1930.

As is well known, poplar wood is one of the most valuable woods for use in the making of wood pulp. At the present time there are known in the United States and foreign countries, according to Illick (1924) and to Sargent (1922), approximately thirty varieties of poplar and five commonly recognized hybrid poplars. Dode (1905) lists 110 species but the accuracy of this is questioned. Only two species of these are commercially useful for pulpwood. The commonly recognized hybrids include the Lombardy poplar (male), Regenerata poplar (female), Carolina poplar (Eugenei) (male) and Robusta poplar (male), the parent trees of which are not definitely known. The fifth of the hybrid poplars known as *P. (Populus) generosa* which was first obtained in England in 1912, had as its male parent *P. trichocarpa* and as its female parent *P. balsamifera virginiana* (sometimes termed *P. angulata*). As stated, these hybrids were known prior to the present invention and are disclaimed as forming no part of the invention.

Due to the increasing consumption of poplar wood in cellulose industries, and the resulting decreasing supply, it is obviously desirable to provide abundant sources of poplar wood for future consumption. However, several disadvantages attend the reforestation of land with ordinary poplars. For example, ordinary poplar species used commercially, such as *P. tremuloides* and *P. grandidentata*, require many years of growth to provide trees of suitable size for supplying wood for use in making wood pulp or for lumber, e. g. a tree 12″ in diameter will ordinarily be 80 years or more old. In addition, for maximum growth of ordinary poplars, a rich soil or the use of fertilizers is required. Further, ordinary poplars are susceptible to numerous common tree diseases, such as cytospora and *Melampsora medusæ*. Finally, the length of fiber of the wood of ordinary poplars is not so great as might be desired for the making of paper pulp, so that a portion of longer fiber pulp (such as that from spruce) is often added to the poplar pulp to give the paper the desired strength.

The present invention overcomes all of the foregoing disadvantages and provides a new variety of hybrid poplar which not only grows quickly in ordinary soil but is particularly suitable for supplying wood of high grade for lumber and for use in making wood pulp.

When two species of the populus genus are crossed seeds are obtained which when grown produce seedlings of varying types. Some of these seedlings will be dwarfs, some will grow at the same rate as their parents, and others will grow so rapidly that, relatively speaking, they partake of the nature of giants. The present invention is concerned with the propagation of those seedlings which are giants, i. e. which have a rapid growth rate. In general, it is found that the varieties which are particularly useful are those whose dimension is more than twice the corresponding dimension of the parent trees. By dimension is meant the height of the tree at the same age, as well as the diameter of the tree at the same age. In some cases, I have found that the hybrid tree produced has a relative dimension as great as three times the corresponding dimension of the parent trees.

In order to obtain seedlings of the desired characteristics as set forth above I have grown approximately 16,000 seedlings obtained by crossing different varieties of poplars and determined which of these hybrid seedlings possessed the characteristics of the desired tree. The better of these seedlings have been propagated vegetatively and the desired characteristics were found to continue and show in the trees so produced vegetatively. This, of course, is frequently not true of subsequent generations grown from seed after a hybrid crossing. A portion of this work has been described in the Journal of Heredity, vol. 24, pages 216–229, in 1933.

Of course, one could not be certain of obtaining trees of the desired characteristics no matter how such work was done. The uncertainty of results is always present in attempting to get by hybridization a particular type of tree. Ordinarily in hybridization one simply makes numerous crosses and picks out the one most interesting. In this particular case, however, I was searching for trees of a particular type and, in general, discarded the hybrids produced unless they partook of the nature of the type for which I was searching. The present application is for a hybrid of which the male parent was *P. berolinensis* and the female parent *P. tacamahacca candicans*, sometimes known as Balm of Gilead, but differing from *P. balsamifera virginiana*, which also is sometimes known as Balm of Gilead.

The method which I have employed in producing the seedlings of the hybrid poplar set forth above consisted in tying paper sacks over the clusters of flowers on the female trees before the flowers had opened in order to prevent normal pollination. Later, when the flowers had opened, pollen was obtained from the flowers of the selected male tree. The pollen was taken at once to the female tree, and by means of a wad of cotton, dusted over the female flowers. The sacks were immediately replaced to prevent normal pollination. After about two weeks the paper sacks were replaced by green cheesecloth sacks.

Approximately six weeks later when the seeds had ripened, they were removed, the cotton carefully picked off and the seed planted in damp sand. When the seeds had germinated and the little trees had reached a height of about two inches, the small trees were transferred to larger containers and separated somewhat. Later, the seedlings were individually planted. At the end of the following summer the seedlings of desired characteristics were selected for propagation.

I have found that by simply taking the cuttings and making a hole approximately eight inches in depth in the damp ground by means of a sharp stick, putting the lower end of a cutting ⅜ inch in diameter and twelve or fourteen inches in length in the hole, and pressing the ground back around the cutting, fully 95 per cent. of the cuttings of the new hybrids will grow. As is known to those skilled in the art, this vitality is not shown by their parents. Indeed, in the case of the common poplar (*P. tremuloides*) for example, not more than one or two in a thousand will grow under the same circumstances.

The general method of progagation applicable to the new hybrid poplar constituting the present invention is as follows: From the seedling tree produced, cuttings of the new wood (the preceding summer's growth or the growth of two summers) are made after the leaves have fallen in the fall. These cuttings may be taken, generally speaking, during the period from November to March. The cutting from the small tree is then divided into pieces approximately from ten to fifteen inches in length. These cuttings are stored in an ice house or similar cool room or placed under ground until the time for planting is at hand. Of course, they must not be allowed to dry out. The cuttings may be planted either in the fall before the ground has become frozen or, as is preferable, in the spring shortly after the frost has left the ground and before the weeds have started to grow vigorously. The cutting is inserted in the ground, where it will begin to grow with considerable rapidity. I have found that, in the latitude of New York, with average summer weather, the cutting of this new variety will grow into a tree about six feet in height by the 15th of September. Under the same circumstances, the pure species which were the parents of this same hybrid will not reach a height of more than two or three feet. The growth of this new hybrid poplar in succeeding years is about the same as during the first year, that is, a gain of about six feet in height and approximately an inch in diameter per year may be counted upon.

I have found that from one cutting there will be obtained in one summer a five to seven foot tree. By cutting this tree into cuttings of say fourteen inches in length, there may be obtained from six to ten cuttings suitable for planting the following year, and from the old stalk there will come up a number of shoots so that during the following year there will be obtained not only the six to ten cuttings (each capable of providing six to ten new cuttings for propagation) but also from the the original stalk sufficient material to furnish another fifteen to twenty cuttings.

As will be apparent, if the tree is not cut up it will grow to be a mature tree and can be expected to increase in diameter nearly an inch per year and in height about six feet per year. The exact increase will be determined by the length of the growing season and by the supply of rain during the particular summer in question. I have found that the new hybrid poplar above referred to thrives on sunshine and rain but requires little in the way of rich soil or fertilizers. Analyses of the wood show that this hybrid poplar, contrary to most trees, does not take up from the soil much more than a trace of nitrogen, potash or phosphates. In fact, attempts to secure the usual effects of fertilizer have failed to show more than about 10 per cent. increase in growth due to fertilizer treatment. In no event has the rate of growth of the herein described hybrid poplar been increased 20 per cent. by the use of fertilizer.

While the above describes the method always used in the early work of propagation of this new hybrid, later work has shown that the method of the McKee Patent No. 1,943,030, Propagation of trees from cuttings, is applicable so that all of the tree except the leaves can be used for propagation and thus a much more rapid multiplication of available trees be provided.

Of the hybrid poplars known previously *P. eugenei* is generally considered as the most rapid growing but it shows annular rings of only about ⅛ inch. The wild poplars, such as *P. tremuloides*, which are now customarily used for lumber and pulpwood purposes show an annular ring of about 1/11 inch. It is, accordingly, evident that the new hybrid described herein has a surprising rate of growth in that it is much more rapid in growing than the pure species, ordinary aspen, *P. tremuloides*, which is considered the fastest growing commercial wood of the northern forests, or the hybrid poplars grown in lumber plantations in Italy and France, *P. eugenei*, which is considered the fastest growing of the hybrid poplars hitherto known.

Figure 2:
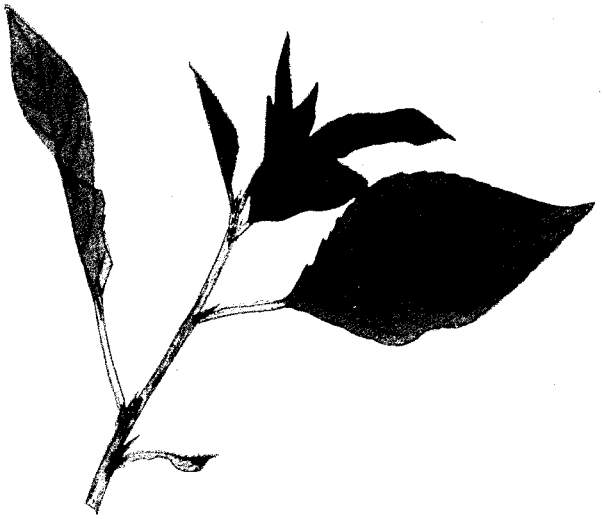

Figure 1 shows chromosomes; Figure 2 shows infantile leaves.

*Chromosomes*

A study of the chromosome numbers as shown in the root system from growing cuttings was made. The stainings were made with the Flemming and Heidenhain stains. In Figure 1 of the original drawing the magnification is 3700 times and the cell represented is from the cortical zone of a root tip stained with Heidenhain stain. The nucleus is in the equatorial plate stage of mitosis and shows 38 chromosomes.

*The buds*

The buds in summer are elongated with sharp tips. They are 6 to 10 mm. long, glossy, dark brown in color, somewhat sticky, aromatic, and compact. In winter the terminal buds are broadly ovoid, and the lateral or lower buds are broad with slightly extended tips. They measure 9 to 14 by 4 to 6 mm., and are medium brown, compact, and not sticky or resinous.

*The leaves*

The mature leaves are ovate with the apex sharp-pointed, at times sharply drawn out from the main part of the blade. The leaf base is blunt to slightly heart-shaped. Its texture is firm, and the color is medium green above, paler below. The margin is rather coarsely scalloped, usually having 2 to 3 scallops per cm., possessing glands, and being wavy in appearance. The veins are green above and below. The midrib and lower parts of the large veins are sparsely covered with minute hairs on the upper surface and even less hairy on the lower. The petiole, or leaf stalk, is slightly flattened, rather bright red and with minute hairs on the upper side, and green with very few hairs below. The leaf stalk possesses lenticels, or "breathing pores", and ranges from 32 to 44 mm. in length. The stipules, or leaf accompanying organs, are awl-shaped, green in color, sharp-pointed, and fall off shortly after their initial appearance.

The leaves of the secondary shoots are ovate or perhaps somewhat narrowed. The apex is sharp with the base blunt to wedge-shaped. The margin is somewhat more finely scalloped, with 3 to 5 scallops per cm., than that of the above described leaves. The veins have fewer hairs than above described.

The juvenile leaves are as dark green as the mature leaves, contrasting sharply with those found in other poplar varieties in which the juvenile leaves are extremely pale.

The infantile leaves are shown in Figure 2 of the original drawing in exact size of the leaves in July from a cutting planted the latter part of May. In color they are also dark green, which is unexpected in such small leaves. When a little older they are usually lanceolate with acute tips and cuneate bases.

*The stems*

The stems are round, the vigorous shoots being slightly ridged toward the tips and beset with downy hairs practically to the base. In winter the shoots are slightly ridged and brownish gray toward the tip, becoming gray nearer the base. In summer the color of the shoots is greenish brown or dull red toward the tip and grayish green nearer the base, and they are somewhat reticulate, i. e. covered with netted raised ridges toward the base. The lenticels, or "breathing pores", in summer are white and narrowly elongated near the tip of the shoots, oval and brownish- or pinkish-white toward the base, measuring 0.5–5.0 mm. in length; in winter their color is grayish white and in shape they tend to be broadly linear near the stem apex, and elliptical to circular toward the base. The secondary shoots are round, without ridges, reddish, and more freely beset with minute hairs. In cross section the pith is five-sided, brown, and of homogeneous consistency. In winter the leaf scars are broadly triangular, with the lower corners turned down, and winged and keeled by low ridges, which are rather sharp except at the leaf scar, where they are rounded. On the upper portion of the stem the ridges extend to the next lower bud. There are three prominent scars representing the ends of fibro-vascular bundles. The scars of the stipules, or leaf-accompanying organs, are prominent, shaped like a narrow half-crescent, and usually somewhat blackened toward the base of the stem.

*Wood*

The density of the wood of the present hybrid is about twenty percent greater as compared with the poplars at present used for lumber and pulpwood (*P. tremuloides, P. grandidentata, P. deltoides,* and *P. eugenei*). This is the more striking as rapid growing trees ordinarily give soft and light woods.

*Resistance to disease*

This new hybrid poplar is not affected by the common poplar diseases. For example, it seems to be entirely immune to cytospora, the most common disease of both the wild and cultivated poplars. It is likewise not affected by *Melampsora medusae,* the red rust that has proven to be a pest to most poplars growing in America, i. e., those designated under the names of *P. tremuloides, grandidentata, angulata, balsamifera, deltoides, wislizeni, occidentalis, dilatata,* and even *candicans.* European poplars are similarly affected.

One would like to have available the flower and seed characteristics but obviously they can not be given as it would require a tree 15 to 20 years old to get these characters in true form. It was felt that it was not safe to attempt to get flowers and seed growth by grafting on mature trees as such growth is often affected by the hormones present in the sap of the grafter tree.

A study of the root producing hormones along the lines of the work done by Wend brings out that this hybrid produces an exceptional amount of such hormones.

The new hybrid poplar which I have developed shows not only a more rapid rate of growth than the parent trees but a greater freedom from the ordinary diseases to which poplars are susceptible. In addition, this hybrid poplar shows an increased length of fiber as compared with that of the parent trees. As is obvious, this greater length of fiber is important, not only because it provides a wood of greater mechanical strength, but even more so because it provides a wood which when used for the making of paper is found to give materially stronger paper. As is well known, greater length of fiber is a decided advantage from the paper making standpoint. The ordinary poplar used for paper making, known as *P. tremuloides,* has, in the case of a one year old plant sampled a foot from the ground, a fiber length averaging about 0.54 mm. whereas the new hybrid set forth above has fiber length under the same conditions of about 0.80 mm. These figures are for small trees in a single summer's growth. Older trees have correspondingly longer length fiber; that is, the same approximate ratios are kept up.

The characteristics of this hybrid are:

(1) Fiber length of over 0.80 mm. in first year's growth.

(2) Growth not increased 20% by fertilizer.

(3) Rapid growth in diameter, e. g., ⅜ inch ring width.

(4) Rapid growth in height, e. g., 6 feet in a year.

(5) Large proportion of the wood in the bole.

(6) Very few branches.

(7) Chromosomes 38.

(8) Resistance to disease.

(9) Ready propagation from cuttings.

There are scarcely any other characteristics that could be named which, from the viewpoint of those engaged in the art of growing trees for pulpwood or lumber, could be as distinctive as the major ones of those listed above, i. e., length of fiber, freedom from disease, speed of growth, and nearly entire lack of fertilizer effect.

From the foregoing it will be seen that I have developed from the parents *P. berolinensis* and

*P. tocamahacoa candicans* a new hybrid poplar which is particularly suitable for supplying wood for lumber and for use in making wood pulp and which, because of the rapid growth rate of the trees and freedom from disease, is particularly valuable for reforestation purposes.

I claim:

A new and distinct variety of poplar as described characterized particularly by its superior size and form, its dark green infantile leaves, its average fiber length of 0.80 mm. in one year old trees, its resistance to disease, and its 38 chromosomes.

RALPH H. McKEE.